United States Patent [19]

Nayak et al.

[11] Patent Number: 4,752,473

[45] Date of Patent: Jun. 21, 1988

[54] EXPRESSION OF GLYCOSYLATED HUMAN INFLUENZA HEMAGGLUTININ PROTEINS

[75] Inventors: Debi P. Nayak; M. Abdul Jabbar, both of Los Angeles, Calif.

[73] Assignee: The Regents of the University of California, Berkeley, Calif.

[21] Appl. No.: 660,441

[22] Filed: Oct. 12, 1984

[51] Int. Cl.$^4$ .................. A61K 39/00; C07K 7/10
[52] U.S. Cl. ........................... 424/88; 530/324
[58] Field of Search ............... 530/395, 324; 435/317; 536/27; 424/88

[56] References Cited

FOREIGN PATENT DOCUMENTS 60057 2/1982 European Pat. Off.

PUBLICATIONS

Nature 289, (1981), 366–373.
Nature 303, (1983), 41–44.
Hitzeman et al., *Science*, vol. 219, pp. 620–625, (2/83).
Kramer et al., *Proc. Natl. Acad. Sci.*, vol. 81, pp. 367–370, (1/84).
Tuite et al., *The Embo Journal*, vol. I, No. 5, pp. 603–608, (1982).
Derynck et al., *IRL Press Ltd.*, vol. II, No. 6, (1983), pp. 1819–1837.
Hitzeman et al., (1981), *Nature* (London), 293, 717–722.
Miyanohara et al., *Proc. Natl. Acad. Sci.*, vol. 80, pp. 1–5, (1/83).
Goff et al., *Gene*, (1984), pp. 35–46.
Ammerer et al., *Nature*, vol. 298, (7/82), pp. 347–350.
Mellor et al., *Gene*, (1983), pp. 1–14.

*Primary Examiner*—Delbert R. Phillips
*Attorney, Agent, or Firm*—Poms, Smith, Lande & Rose

[57] ABSTRACT

Glycosylated polypeptides corresponding to antigenic portions of mature human influenza hemagglutinin are microbially produced in *S. cerevisiae*. The glycosylated polypeptides are effective as vaccination agents, since the glycosylated polypeptides closely minic the naturally occurring mature influenza hemagglutinin which is also glycosylated.

5 Claims, 1 Drawing Sheet

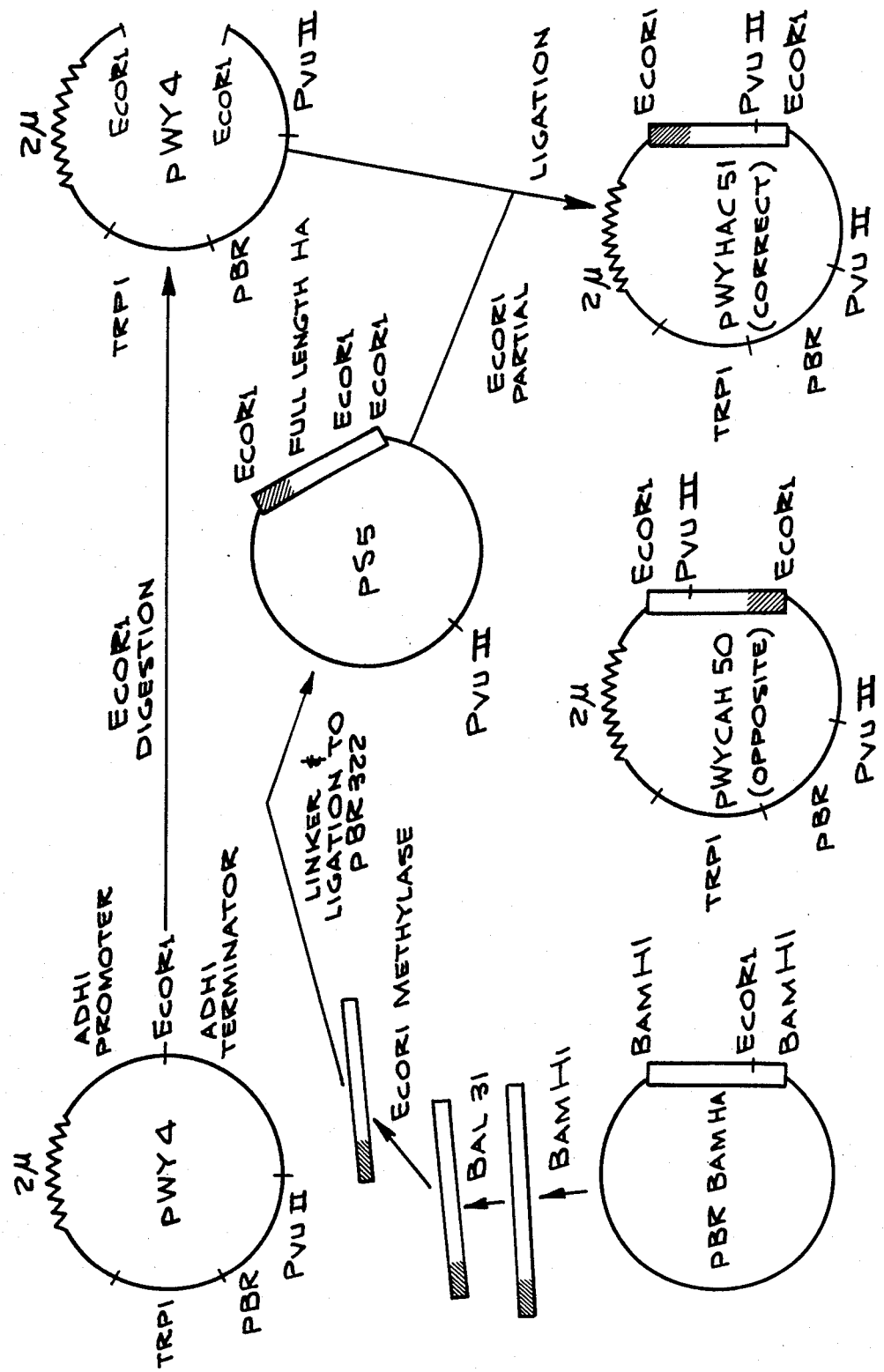

EXPRESSION OF GLYCOSYLATED HUMAN INFLUENZA HEMAGGLUTININ PROTEINS

BACKGROUND OF THE INVENTION

The present invention relates generally to the production of human influenza hemagglutinin proteins in baker's yeast, Saccharomyces Cerevisiae employing recombinant DNA technology. More particularly, the present invention relates to the production in yeast of glycosylated human influenza hemagglutinin proteins which mimic native influenza hemagglutinin proteins present in humans and animals to thereby provide a potentially effective vaccination agent.

The publications and other reference materials referred to herein to describe the background of the invention and to provide additional detail regarding its practice are hereby incorporated by reference. For convenience, the reference materials are numerically referenced and grouped in the appended bibliography.

The influenza virus is a well known human and animal pathogen which causes pandemics and major epidemics in humans and animals. Although the disease is usually relatively mild in healthy individuals, it can be quite serious in elderly individuals and/or those who have chronic physical ailments. In addition to pain and suffering, the financial losses from lost work time due to influenza epidemics are quite substantial. Accordingly, the prevention of outbreaks of influenza is of great economic and social value.

Influenza is caused by a virus vector which invades and infects host organism cells, disrupting their useful functions. Vaccines prepared from killed or attenuated influenza virus have been in use since the early 1940's. These conventional vaccines are usually prepared from chick embryos in which the virus is grown. Live virus is subsequently killed before it is used as a vaccine. Since the whole virus is used in vaccination, numerous problems have resulted from the use of such vaccines, including adverse side reactions, toxic effects and other problems inherent in the production of a vaccine from the killed or attenuated virus. Accordingly, there has been a great deal of interest in developing an effective vaccine against influenza which does not require the use of whole virus either attenuated or killed.

The influenza virus is a segmented negative strand enveloped RNA virus which codes for at least 10 proteins. Three of the proteins are the membrane proteins: hemagglutinin (HA), neuraminidase (NA), and matrix protein (M) (1). These membrans proteins are assembled into virus particles during maturation of virus as it "buds" through the host-cell membrane. Of the three membrane proteins, HA and NA are integral membrane glycoproteins.

Recently, a great deal of interest has been generated in studying both HA and NA. Their primary as well as 3 dimensional structure have been determined (57,58). However, HA is quantitatively the major surface glycoprotein of influenza virus (2) and the antigen against which neutralizing antibodies are elicited (3, 4).

HA of the A/Hong Kong/1968 virus is a trimer of 224,640 molecular weight (MW). It may be solubilized from the viral membrane by bromelain digestion, which removes a 5,406 MW C-terminal hydrophobic (anchoring) peptide from each subunit. This observation, extended by the results of subsequent primary sequencing experiments places the hemagglutinin in a class of integral membrane proteins characterized by a three-domain structure with a large hydrophilic, carbohydrate-containing domain on the external surface of the membrane, a small, uncharged hydrophobic peptide of 24–28 amino acids spanning the membrance, and a small, hydrophilic domain (10–55 amino acids) on the internal side of the membrane (57).

The HA chain is typical of membrane glycoproteins and is initially synthesized as an immature polypeptide including an N-terminal hydrophobic signal peptide. The signal is subsequently removed as part of the process by which the polypeptide is transported across and anchored into the membrane as the mature polypeptide. Each polypeptide chain of the mature trimer is glycosylated at seven sites with a total carbohydrate of 13,000 MW (19% by weight) (57). The glycosylation sites are found in the HA where there is an amino acid triplet beginning with asparagine and ending with either threonine or serine. The sites are located at amino acids Nos. 11-13, 56-58, 125-127, 268-270, 480-482 and 539-541. In higher animals, the sugars are first attached in rough endoplasmic reticulum and further processed, and new sugar molecules are attached in Golgi complex. These sugars are attached at the glycosylation sites and the native hemagglutinin contains fucose, galactose, high mannose, glucose, sialic acid and other complex sugars.

The advent of recombinant DNA techniques has aided greatly in our understanding of the structural features that determine the biological and antigenic properties of the HA of influenza virus (5, 6, 7). As a result of the development of recombinant DNA techniques, polypeptides corresponding to the mature HA protein have been expressed in Escherichia coli (8,9, 10). The microbial production of HA in E. coli has generated a great deal of interest in utilizing the recombinant HA as subunit vaccines against influenza (11).

Laver et at., :The Antigenic Sites on Influenza Virus Hemagglutinin. Studies on Their Structure and Variation," Structure and Variation Influenza Virus, Supra., p. 295, and Wiley et at., Nature, 289, 373 (1981), report on the amino acid sequences of importance with respect to antigen determinants. Specifically, based upon their work, it can be predicted, in general, that amino acides 30 to 275 of the mature hemagglutinin protein contain at least one and probably the most important of the several antigenic determinants. Specifically, they show that amino acides 140 to 146 of A/Memphis/102/72 (H3) represent a site important for an antigenic determinant. This corresponds in structure to amino acids 153 to 159 A/WSN/33 (H0). In accordance with the present invention, it is possible to express each of the human influenza hemagglutinin polypeptides, or proteins thereof which contain at least one antigenic determinant site, located as defined above.

Co-pending U.S. patent application No. 239,301 was filed on Mar. 2, 1981 and is assigned to the same assignee as the present application.

In this application, various plasmid vectors are disclosed which code for polypeptides corresponding to antigenic portions of mature HA (i.e., HA without the signal peptide). The plasmids are used to transform E. coli to express the hemagglutin polypeptides which were demonstrated to be useful as vaccination agents. The mature HA expressed by E. coli is not glycosylated due to E. coli's inherent inability to produce glycoproteins.

Since one of the goals of a vaccine is to mimic the natural state of the viral antigen as closely as possible, it would be desirable to produce an HA polypeptide which is glycosylated to thereby provide as close a resemblance as possible, both structurally and immunologically, to the native HA of influenza.

SUMMARY OF THE INVENTION

In accordance with the present invention, it has been discovered that glycosylated polypeptides corresponding to antigenic portions of mature HA can be expressed in *Saccharomyces Cerevisiae* (*S. cerevisiae*). These glycosylated peptides were demonstrated to be reactive with antibodies raised against influenza virus and therefore are potentially useful as vaccination agents.

The present invention is based on the discoveries that plasmid vectors coding for the HA protein, including the signal peptide, can be used to transform *S. cerevisiae* to express HA polypeptide precursors which include the signal prepeptide and that *S. cerevisiae* is capable of processing the polypeptide precursors to produce matrue glycosylated HA polypeptides which lack the signal prepeptide. The production of such glycosylated HA provides a convenient and effective means for microbially producing HA polypeptides which more closely resemble naturally occurring mature HA than the non-glycosylated polypeptides expressed in *E. coli*. Accordingly, the glycosylated polypeptides produced in accordance with the present invention will be more effective as a vaccination agent. Further, *E. coli* may produce endotoxins which must be removed from the expressed polypeptide products prior to their use as pharmaceutical or vaccination agents. The glycosylated polypeptides expressed in *S. cerevisiae* are likely to be toxin free and therefore is less likely to produce adverse side effects.

The above discussed and many other features and attendant advantages of the present invention will become better understood by reference to the following detailed description when considered in conjunction with the accompanying drawings.

BRIEF DESCRIPTION OF THE DRAWING

The drawing is a schematic outline of the synthesis of an exemplary expression vector in accordance with the present invention.

DETAILED DESCRIPTION OF THE INVENTION

The present invention basically invovles the production of glycosylated polypeptides in *S. cerevisiae* which correspond to known antigenic regions of mature HA and therefore are useful as vaccination agents to raise antibodies in humans and animals to combat influenza virus attacks. The present invention is based upon the transformation of *S. cerevisiae* with suitable plasmids or other cloning vehicles to produce transformed *S. cerevisiae* which expresses polypeptides that are glycosylated with high mannose type sugars and correspond to antigenic regions of the mature HA protein. Although numerous different plasmids may be used to transform the *S. cerevisiae* in accordance with the present invention, the following description will be limited to an exemplary preferred process in which a two micron based yeast shuttle plasmid vector which is compatible with *E. coli* and *S. cerevisiae* is used.

As set forth in the previously mentioned co-pending patent application, the hemagglutinin gene of WSN virus has been cloned (35) and its complete nucleotide sequence determined (36). The sequence of the hemagglutinin HA gene A/WSN/33 strain (H1H1) of human influenza virus has been compared with four other typical HA sequences: the human H2 strain A/Japan/305/5/57, the human H3 strains A/Memphis/102/72 and A/Victoria/3/75 and HAV 1 (fowl plague). Details concerning this work are described in Ref. 36. Also see the previously referred to co-pending patent application Ser. No. 239,301, the contents of which is also incorporated by reference.

The A/WSN/33 HA gene is 1775 nucleotides in length and codes for 565 amino acids. The cRNA contains a 5' noncoding region of 32 nucleotides, a coding region of 1695 nucleotides and a 3' noncoding region of 48 nucleotides. The sequence shows a 17 amino acid signal prepeptide at the amino terminus followed by HA1 (325 amino acids), a single arginine connecting residue, and HA2 (222 amino acids) at the carboxy terminus. The sequence contains, at amino acids 153-159, a tryptic peptide shown to be changed in variants of H1N1 virus (A/PR8/34) selected with monoclonal antibodies, indicating that this region is an antigenic determinant.

A two micron based yeast shuttle plasmid vector containing ADHI promoter and terminator which is identified as pWY4 was obtained from Wyeth Laboratory, Philadelphia, Pa. Conventional restriction endonuclease digestion and ligation with T4 DNA ligase were conducted as recommended by the suppliers to provide an expression vector encoding for the entire HA protein including the signal peptide and the HA1 and HA2 segments. pWY4 expression vectors encoding for HA protein without the signal peptide (signal minus) were also prepared.

The strategy for the construction of the complete HA expression vector is outlined schematically in FIG. 1. The junction sequence of the promoter and the hemagglutinin genes is as follows:
ADHI Promoter (CAAGCTATACCAAGCATACAACTATCT)—EcoR1 linker (GGAATTC-C)—HA non-coding region (AAAAACAACAAA)—Initiation codon (AUG-)—signal peptide (AAGGCAAAACUACUGGUC).

The junction sequence for the signal minus HA was the same except that a synthetic initiator codon (ATG) was inserted before the codon for Asp (GAC) of mature hemagglutinin (9). Also, the signal peptide sequence is deleted and the amino terminal of HA1 (GACACAAUAUGU, etc) is connected directly to the initiation codon.

As shown in the drawing, Ba131 digestion was carried out to remove the first 14 nucleotide residues, including guanosine residues number 11-14, (35) in the non-coding region of the HA, as they may interfere with efficient translation initiation in yeast (37). Subsequently, the HA DNA fragment was treated with EcoR1 methylase to protect the internal EcoR1 site. EcoR1 linkers were added and cloned into EcoR1 site of pBR322. The full length HA insert was obtained by partial EcoR1 digestion and the insert was then cloned into EcoR1 site of pWY4. pWY4 is a shuttle vector which can replicate both in *E. coli* and in yeast, *S. cerevisiae*.

In order to amplify the pWY4 vector vehicle, *E. coli* 294 was transformed with the recombinant pWY4 plasmids carrying the HA inserts. *E. coli* 294 (end-A, thi, hsdR) was used for plasmid transformation and isolation (24). Composition of LB medium and growth conditions of *E. coli* cell have been described (25). Ampicillin resistant colonies containing recombinant plasmids were identified and the clones were further screened for the orientation of the HA inserts. A plasmid containing the correct orientation of HA cDNA insert was named pWYHAC51 and the one in the opposite orientation, pWYCAH50. A similar procedure for constructing a recombinant plasmid containing cDNA insert of the signal minus HA under the control of ADHI promoter was used. For the initial construction of signal minus HA, a synthetic DNA primer was used to remove the sequences encoding the hydrophobic amino acids of signal sequences and to add a synthetic ATG initiation codon before ASP codon of the mature HA polypeptide. The detailed strategy of this construction has been described elsewhere (9). The correct and opposite orientation plasmids for signal minus HA are named pWYHAS1 and pWYSAH2, respectively. The sequences at the junction of both plasmids were determined by DNA sequencing method of Maxam and Gilbert (38).

S. cerevisiae 20B-12 (α, trp-1, gal-7, SUC, pep 3-2 ) (26) was used as recipient for transformation by recombinant yeast plasmids. The composition of minimal medium (SD) and rich (YPD) medium has been described (27). The yeast 20B-12 and its transformant derivatives were grown at 30° C. in appropriate media as required by specific experimental needs. The yeast transformants (Trp+) were grown in synthetic dextrose (SD) selective meidum supplemented with uracil (20 μg/ml), adenine (20 μg/ml), tyrosine and phenylalanine (50 μg/ml) until midexponential phase $A_{600}=1.0-1.5$). The cells were centrifuged and resuspended in fresh SD selective medium at an $A_{600}=2.0$. [$^{35}$S] methionine was added to the cells at a concentration of 100 μCi/ml and labeled at 37° C. for two hours. At the end of the labeling period, the cells were spun down and washed once with 5 ml of 10 mM NaN$_3$ solution. The lysis of cells and immunoprecipitation with anti WSN antiserum were done essentially as described elsewhere (30) exept that protein-A Sepharose was used to collect the immune complexes. The immune complexes were washed according to Julitus et al (30) and final washed pellets were resuspended in 50-100 μl of gel electrophoresis sample buffer (60 mM Tris-HCl pH 7.0; 10% glycerol; 2.5% SDS; 0.05% BPB; 0.5M β-mercapteoethanol) before boiling them for 3 minutes. Samples were clarified by centrifugation in a microfuge for 5 minutes and portions (4000-16,000 cpm) of the supernatant fluids applied to the sample wells of polyacrylamide slab gels for separation and identification of the immune complexes.

Spheroplasts were isolated and extracts prepared as follows:

The yeast transformants (Trp+) were grown in supplemented SD selective medium to an $A_{600}$ of 1.5. 10 ml of the labeled cells were centrifuged and suspended in 4 ml solution of spheroplast buffer (1.2 M sorbitol, 50 mM phosphate pH 7.2, 15 mM β-mercaptoethanol and zymolyase (60,000 μ/g)(100 μg/ml) and were incubated for one hour at 30° C. with gentle shaking (18). The spheroplasts were spun down at 1200 rpm for 10 seconds and washed three times with 6 ml of spheroplast buffer without zymolyase (31). The collected spheroplasts were lysed by adding 1 ml of 1× PBS in the presence of 1 mM PMSF on ice for 30 minutes. The pellet fraction (membrane) was collected by spinning the lysed spheroplast at 5000 xg for 20 minutes (32). The membrane fractions were solublised in SDS as described (30), after washing them once in 2 ml of 1× PBS.

Expression of the virus HA from the Chimeric plasmids:

Since all the recombinant plasmids carry wild type trp allele, tryptophan independent transformants of the yeast 20B-12 were obtained by transformation with these plasmids. The yeast transformants that harbor the plasmids, pWYHAC51 and pWYCAH50, were labeled with [$^{35}$S]-methionine and the proteins were analyzed on the 10% PAGE-SDS gels. Autoradiograms were made of the polypeptides immunoprecipitated with rabbit anti-WSN antibodies (purified by preabsorbing the antibodies with yeast extract made from SEY2102 (39). Both yeast extracts (pWYHAC51 and pWYCAH 50) when immunoprecipitated contain a number of protein bands. These bands would probably represent yeast specific polypeptides which were immunoprecipitated by rabbit serum. Similar nonspecific immuniprecipitation has been observed by others. However, in addition to these common polypeptides, the WSN antibodies also precipitated a specific broad heterodisperse polypeptide band from the lysate of 20B-12/pWYHAC51. This polypeptide band was completely absent in the lysate of 20B-12/pWYCAH50, the plasmid containing HA in the wrong orientation, indicating that the plasmid pWYHAC51 directs the synthesis of the specific polypeptide that should be HA. Furthermore, the HAC 51 polypeptide migrated at the same position as the HA made in Madin-Darby Bovine Kidney (MDBK) cells infected with WSN virus. Also, a number of independently isolated HAC 51 transformants also exhibited the same polypeptide bands after immunoprecipitation, but none of the CAH 50 transformants (opposite orientation) demonstrated the presence of the HA specific polypeptide (data not shown).

Furthermore, to test the association of HA polypeptides with pWYHAC51 plasmids, a number of segregants which are cured of the plasmid pWYHAC51 were isolated. If yeast cells carrying a plasmid with a 2 micron circle origin are propagated nonselectively, segregational loss of the plasmid occurs very frequently (28). When the transformants were cured of pWYHAC51 by growing them nonselectively in rich yeast extract, peptone and destrose (YPD) medium, each (5 of them tested) of the tryptophan requiring segregants that were tested also failed to produce the HAC51 polypeptide (data not shown). This clearly indicates that the HAC 51 polypeptide is plasmid-borne.

Similarly, the plasmids bearing the signal minus HA in both orientations were also introduced into the yeast 20B-12 and the proteins, immunoprecipitated by antiviral rabbit antibodies, were analyzed in those transformant cells. The signal minus HA appears to be expressed in yeast transformed with plasmid pWYHA1; however, the protein band was sharper and migrated faster than the broad heterodisperse polypeptide made in the yeast transformants (20B12/pWYHAC 51) carrying the complete HA insert.

The heterodisperse band which appeared in cells transformed with plasmids carrying full length HA (pWYHAC51) is believed to be due to the glycosylated form of HA, since in yeast S. cerevisiae secretory and other glycoproteins are shown to be glycosylated as they pass through the organelle-dependent pathway (12). S. cerevisiae has been shown to produce N-linked glycosyl chains identical in structure to the mannose-rich core oligosaccharides attached to aspargine residues in mammalian glycoproteins (40, 41, 42, 43). However, in mammalian systems, complex sugars are added to the glycoproteins at a later step during protein transport, in contrast to the yeast system where only high mannose sugars are added (44,45). Since HA produced in yeast is indeed glycosylated, the protein portion of the molecule can be produced with concomitant reduction in $M_r$ by treatment with endoglycosidase H (endo H) which cleaves the carbohydrate side chain of the high mannose type but not the complex carbohydrate side chain (46, 47). Accordingly, immunoprecipitate from 20B-12/pWYHAC51 cells was exhaustively digested with endo H to remove N-linked carbohydrate chains from the peptide backbone (48). The immunoprecipitated samples to be digested with endo H were removed from protein-A Sepharose by heating in 20 μl of 1% SDS in boiling water bath, diluted by the addition of 180 μl $H_2O$, heated again for one minute and clarified by centrifugation. 5 μl of Endo H (33 ng/ml) was added to the immune complexes and the treatment continued as described (30). 50 microliter samples were dried in a centrifugal concentrator (Savant Speed Vac) before applying them in a polyacrylamide gel.

PAGE—SDS of the dried samples were performed in slab gels of 10% polyacrylamide (33). Gels were fixed in a solution of 10% acetic acid (w/v), 10% trichloroacetic acid (w/v), 30% methanol (w/v) for 30–45 minutes with constant agitation. Fixed gels were washed twice with $H_2O$ (30 minutes each time) and then permeated with 1 M sodium salicylate for fluorgraph as described elsewhere (34). Gels were dried on filter paper and were subjected to autoradiography using Kodak XAR-5 film at −76° C.

The endo H treatment of the 20B-12/pWYHAC51 immunoprecipitate produces a discrete protein band which moves slightly slower during PAGE-SDS than the signal minus HA which is unaffected by the endo H digestion treatment. The slower mobility could probably be due to two or three sugar residues still remaining on the protein after endo H treatment. These results demonstrate clearly that the viral hemagglutinin coded for by the pWYHAC51 plasmid is glycosylated in yeast the same way several resident secretory and other glycoproteins are glycosylated in that organism. Further, the results show in accordance with the present invention that the signal peptide must be coded for by the plasmic vector in order for glycosylated HA to be expressed by S. cerevisiae.

Sequence analysis of HA of influenza virus A indicates that the polypeptide consists of a hydrophobic signal peptide at the amino terminus of the molecule and another hydrophobic region of 24–27 amino acids at the carboxyl terminus (36, 49, 50). In mammalian cells, the full length HA is expressed, glycosylated and exported to the cell surface (5, 7, 51, 52). It is believed that the HA made in yeast is processed the same way as in the eukaryotic cells and therefore it is probably membrane associated. Immunoprecipitation of various fractions of the cells harboring the plasmid pWYHAC51 was performed. Both mechanical and enzymatic fractionation procedures were employed to analyze the localization of the hemagglutinin.

From the above tests, the HA appears to be predominantly localized in the membrane of the yeast cells. However, mechanical breaking of the cells does not clearly fractionate the HA into membrane or cytosolic fractions even though in the membrane fraction, there seems to be more HA present than in the soluble fraction, considering the amount of radioactivity put on the gels. On the other hand, the enzymatic separation clearly identifies the hemagglutinin in the membrane since no or little HA is detected in the cytoplasmic or periplasmic fractions. These observations indicate that the hemagglutinin made in yeast is processed in a manner similar to one that occurs in higher euharyotic systems. Therefore, it shows that the glycosylation sites on the HA are recognized by the yeast glycosylation system in a manner similar to that of higher eukaryotic organisms. The expected glycosylation sites on the yeast expressed HA are therefore expected to be the same as those mentioned in the Background of the Invention.

Immunocompetition of yeast expressed HA with the natural viral HA was performed in order to confirm that the hemagglutinin made in yeast is antigenically related to viral HA. The yeast cells harboring the plasmid pWYHAC51 were labeled and the lysate made as described (30). The lysate of MDBK cells infected with WSN was the source of competing antigen. The immunoprecipitation of the HA in yeast is competitively inhibited by the unlabeled viral HA demonstrating that the HA produced in yeast contained the antigenic determinant of the native viral HA.

As is apparent from the above description, the glycosylated HA proteins in accordance with the present invention are useful as vaccines for the prevention and/or treatment of human influenza. The vaccines of the present invention, incorporating a polypeptide of HA protein, expressed as herein described, can be prepared according to known methods, where the polypeptide hereof is combined in admixture with a pharmaceutically acceptable vehicle. Suitable vehicles and their formulation are described in Remington's *Pharmaceutical Sciences* by E. W. Martin, which is hereby incorporated by reference. Such vaccines will contain an effective amount of the polypeptide hereof together with a suitable amount of vehicle in order to prepare an effective vaccine for effective administration to the host. Attention is also directed to *New Trends and Developments in Vaccines*, Editors: A Voller and H. Friedman, University Park Press, Baltimore, 1978, which is hereby incorporated by reference, for further background details on the preparation of vaccines.

Such a vaccine is likely to be free of other viral and cellular components and is therefore less likely to produce pyrogenic reaction, Guillain-Banné syndrome, and other complications of whole killed or attenuated virus vaccine preparations.

Although the present invention has been described in terms of using specific strains of yeast cells as the host organism, the invention also covers the use of other strains of yeast cells, which are capable of metabolically processing a precursor protein having a signal peptide to express glycosylated proteins in which the signal peptide has been removed.

The above examples have been limited to embodiments where the entire HA protein is coded for and the glycosylated (signal free) complete protein expressed. It is not necessary that the entire HA sequence be coded for and expressed, so long as the signal peptide is coded for and at least one antigenic determinant coded for. Expression of incomplete HA antigenic determinants present in the HA1 chain are discussed in detail in the co-pending patent application which has previously been incorporated by reference. By suitable recombinant DNA techniques, these same antigenic polypeptide chains can be expressed in yeast, if desired, instead of the entire sequence as herein described.

Having thus described exemplary embodiments of the present invention, it should be noted by those skilled in the art that the within disclosures are exemplary only and that various other alternatives, adaptations and modifications may be made within the scope of the present invention. Accordingly the present invention is not limited to the specific embodiments as illustrated herein, but is only limited by the following claims.

APPENDIX

1. Lamb, R. A. (1983) in *Genetics of Influenza Virus* eds. Palease, P. and Kingsbury, D. W. (Springer-Verlag Wien, N.Y.) pp. 21-69.
2. White, D. O. (1974) *Curr. Top. Microbiol. Immunol.* 63, 1-48.
3. Drzeniek, R., Seto, J. T. and Rolt, R. (1966) *Biochim. Biophys. Acta.* 128, 547-558.
4. Laver, W. G. and Kilbourn, E. D. (1966) *Virology* 30, 493-501.
5. Hartman, J. R., Nayak, D. P. and Fareed, G. C. (1982) *Proc. Natl. Acad. Sci. USA* 79, 233-237.
6. Gething, M. J. and Sambrook, J. (1982) *Nature* (London) 300, 598-603.
7. Sveda, M. M., Markoff, L. J. and Lai, C. J. (1982) *Cell* 30, 649-659.
8. Emtage, J. S., Tacon, W. C. A., Eatlin, G. H., Jenkins, B., Porter, A. G. and Carey, N. H. (1980) *Nature* (London) 283, 171-174.
9. Davis, A. R., Nayak, D. P., Ueda M., Hiti, A. L., Dowbenko, D. and Kleid, D. G. (1981) *Proc. Natl. Acad. Sci. USA* 78, 5376-5380.
10. Heiland, I. and Gething, M. J. (1981) *Nature* (London) 292, 851-852.
11. Nayak, D. P., Davis, A., Bos, T., Ueda, M. and Sivasubramanian, N. (1983) in *Modern Approach to Vaccines*, eds. Lerner, R. and Channock, R. M., (Cold Spring Harbor Laboratory, Cold Spring Harbor, N.Y.).
12. Schekman, R. (1982) *Trends Biochem. Sci.* 7, 243-246.
13. Hitzeman, R., Hagie, F. E., Lavine, H. L., Goeddel, D. V., Ammerer, G. and Hall, B. D. (1981) *Nature* (London) 293, 717-722.
14. Tuite, M. F., Dobson, M. J., Roberts, N. A., King, R. M., Burke, D. C., Kingsman, S. M. and Kingsman, A. J. (1982) *EMBO J.* 1, 603-608.
15. Kramer, R. A., DeChiara, T. M., Schaber, M. D. and Helliker, S., (1984) *Proc. Natl. Acad. Sci. USA* 81, 367-370.
16. Derynck, R., Singh, A. and Goeddel, D. V. (1983) *Nucl. Acids. Res.* 11, 1819-1837.
17. Valenzuela, P., Medina, A., Rutler, W. J., Ammerer, G. and Hall, B. D. (1982) *Nature* (London) 298, 347-350.
18. Miyarohara, A., Toh-e, A., Noaki, C., Hamada, F., Ohtomo, N. and Matsubara, K. (1983) *Proc. Natl. Acad. Sci. USA* 80, 1-5.
19. Mellor, J., Dobson, M. J., Roberts, N. A., Tuite, J. S., Emtage, J. S., White, S., Lowe, P. A., Patel, T., Kingsman, A. J. and Kingsman, S. M. (1983) *Gene* 24, 1-14.
20. Goff, C. G., Moir, D. T., Kohno, T., Gravius, T. C., Smith, R. A., Yomasaki, E. S. and Taunton-Rigby, A., (1984) *Gene* 27, 35-47.
21. Hitzeman, R. A., Leung, D. W., Perry, L. J., Kohr, W. J., Levine, H. L. and Goeddel, D. V. (1983) *Science* 219, 620-625.
22. Edens, L., Bom, I., Ledeboer, A. M., Maat, J., Tooner, M. Y., Visser, C. and Verrips, C. T. (1984) *Cell* 37, 629-633.
23. Goeddel, D. V., Leung, D. W., Dull, T. J. Giross, M., Laiver, R. W., McCandliss, R., Seeburg, P. H., Ullrich, A., Yelverton, E. and Gisay, P. W. (1981) *Nature* (London) 290, 20-26.
24. Bolivar, F. and Beckman, K. (1979) *Methods in Enzymol.* 68, 245.
25. Miller, J. H. (1972) *Experiments in Molecular Genetics* (Cold Spring Harbor Laboratory, Cold Spring Harbor, N.Y.).
26. Jones, E. W. (1976) *Genetics* 85, 23-33.
27. Sherman, F., Fink, G. R. and Lawrence, C. W. (1979) *Methods in Yeast Genetics* (Cold Spring Harbor Laboratory, Cold Spring Harbor, N.Y.).
28. Botstein, D., and Davis, R. W., (1982) in *Molecular Biology of the Yeast Saccharomyces: Metabolism and Gene expression* eds.
29. Mariatis, T., Fritsch, E. F. and Sambrook, J. (1982) *Molecular Cloning: A Laboratory Manual* (Cold Spring Harbor Laboratory, Cold Spring Harbor, N.Y.).
30. Julius, D., Schehman, R. and Thorner, J. (1984) *Cell* 36, 309-318.
31. Van Solingen, P. and VanderPlaat, J. B. (1977) *J. Bacleriol.* 130, 946-947.
32. Marriot, M. S. (1975) *J. Gen. Microbiol.* 86, 115-132.
33. Laemmli, U. K. (1970) *Nature* (London) 227, 680-685.
34. Chamberlin, J. P. (1979) *Analyt. Biochem.* 98, 132-135.
35. Davis, A. R., Hiti, A. L. and Nayak, D. P. (1980) *Gene* 10, 205-218.
36. Hiti, A. L., Davis, A. R. and Nayak, D. P. (1981) *Virology* 3, 113-124.
37. Ammerer, G., Hitzeman, R., Hagie, F., Barta, A. and Hall, B. D. (1981) in *Recombinant DNA Proceedings of the Third Cleveland Symposium on Macromolecules* ed Walton, A. G. pp. 185-197.
38. Maxam, A. M. and Gilbert, W. (1980) *Meth. Enzymol.* 65, 499-500.
39. Emr, S. D., Schekman, R., Flessel, M. C. and Thurner, J. (1983) *Proc. Natl. Acad. Sci USA* 80, 7080-7084.
40. Prakash, C., Katial, A. and Vijay, I., (1983) *J. bacteriol.* 153, 895-902.
41. Zhang, W. J., Cohen, R. E. and Ballou, C. E. (1982) *Fed. Pro.* 41, 887.
42. Hauffker, T. and Robbins, P. (1982) *J. Biol. Chem.* 257, 3202-3210.
43. Byrd, J. C., Tarentino, A. L., Maley, F., Atkinson, P. H. and Trimble, R. B. (1982) *J. Biol. Chem.* 257, 14657-14666.
44. Ballau, C. E. (1982) in *The Molecular Biology of the Yeast Saccharomyces: Metabolism and Gene Expression* eds Strathern, J. N., Jones, E. W. and Broalt, J. R. (Cold Spring Harbor Laboratory, Cold Spring Harbor, N.Y.).
45. Reading, C. L., Panhoet, E. E. and Ballau, C. E. (1978) *J. Biol. Chem.* 253, 5600-5612.
46. Robins, P. W., Hubbard, Turco, S. J. and Wirth, D. (1977) *Cell* 12, 893-900.
47. Tarentino, A. L. and Maley F. (1974) *J. Bio Chem.* 249, 811-817.
48. Tarentino, A. L., Plummer, T. H. and Maley, F. (1974) *J. Biol. Chem.* 249, 5786-5794.

49. Porter, A. G., Barber, C., Carey, N. H., Hallewell, R. A., Threlfall, G. and Emtage, J. S. (1976) *Nature* (London) 282, 471–477.
50. Gething, M. J., Bye, J., Skehel, J. and Waterfield, M. (1980) *Nature* (London) 301–306.
51. Sueda, M. M. and Lai, C. J. (1981) *Proc. Natl. Acad. Sci. USA* 78, 5488–5492.
52. Gething, M. J. and Sambrook, J. (1981) *Nature* (London) 293, 620–625.
53. Davis, A. R., Bos, T., Ueda, M., Nayak, D. P., Dowbenko, D. and Compans, R. W. (1983) *Gene* 21, 273–284.
54. Smith, G. L., Murphy, B. R. and Moss, B. (1983) *Proc. Natl. Acad. Sci. USA* 80, 7155–71.
55. Novick, P., Field, C. and Schekman, R. (1980) *Cell* 21, 205–215.
56. Novick, P., Ferro, S. and Schekman, R. (1983) *Cell* 25, 461–469.
57. Wilson, I. A., Shekel, J. J. and Wiley, (1981) D. C. *Nature* 289, 366–372.
58. Colman, P. M., Varghese, J. N., and Laver, W. G. (1983) *Nature* (London) 303, 41–44.

What is claimed is:

1. A glycosylated polypeptide of human or animal influenza hemagglutinin protein comprising an amino acid sequence selected from the HA1 or HA2 segment of the hemagglutinin protein wherein said amino acid sequence includes at least one antigenic determinant of said hemagglutinin protein, said amino acid sequence including one or more glycosyl groups consisting essentially of high mannose sugars produced in yeast.

2. The glycosylated polypeptide according to claim 1 wherein said glycosylated polypeptide is microbially produced by *S. cerevisiae*.

3. A glycosylated polypeptide according to claim 1 wherein said amino acid sequence is selected from the amino acid sequence corresponding to the HA1 segment of human influenza.

4. A vaccine for use in treating human and animal influenza comprising a glycosylated polypeptide according to claim 1 in admixture with a pharmaceutically acceptable carrier.

5. A vaccine according to claim 4 wherein said amino acid sequence comprises the amino acids corresponding to the HAI and HA2 segments of the hemaglutinin protein.